United States Patent [19]

Casagrande et al.

[11] Patent Number: 5,013,753
[45] Date of Patent: May 7, 1991

[54] PRODRUGS OF DOPAMINE

[75] Inventors: Cesare Casagrande, Arese; Francesco Santangelo, Milan, both of Italy

[73] Assignee: Simes, Vicenza, Italy

[21] Appl. No.: 386,106

[22] Filed: Jul. 28, 1989

[30] Foreign Application Priority Data

Jul. 29, 1988 [IT] Italy .................. 21543 A/88

[51] Int. Cl.$^5$ ............................................. A61K 31/27
[52] U.S. Cl. .................... 514/512; 514/548;
514/538; 560/40; 560/73; 560/109; 560/136;
560/142; 558/269; 558/271
[58] Field of Search ............... 558/271, 269; 560/40,
560/73, 109, 136, 142; 500/109.40; 514/563,
512, 548, 538

[56] References Cited

U.S. PATENT DOCUMENTS

| | | | |
|---|---|---|---|
| 3,891,696 | 6/1975 | Bodor et al. | 560/40 |
| 3,947,590 | 3/1976 | Kyncl et al. | 514/563 |
| 4,105,787 | 8/1978 | Jones et al. | 514/533 |
| 4,125,626 | 11/1978 | Orlowski et al. | 514/566 |

*Primary Examiner*—James H. Reamer
*Attorney, Agent, or Firm*—Stevens, Davis, Miller & Mosher

[57] ABSTRACT

Compounds of formula

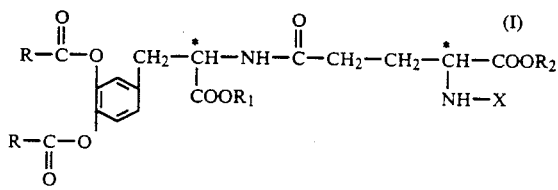

(wherein R, $R_1$, $R_2$ and X have the meanings reported in the specification), the processes for their preparation and the pharmaceutical compositions containing them as active ingredient are described.

The compounds of formula I are useful in the treatment of Parkinson's disease, renal failure, cardiac decompensation and hypertension.

4 Claims, No Drawings

PRODRUGS OF DOPAMINE

The present invention relates to prodrugs of dopamine and, more particularly, it relates to derivatives of gamma-glutamyl-L-dopa with high bioavailability by oral route.

Dopamine is a natural catecholamine having important pharmacological effects on the central nervous system and on the renal and cardiovascular system which are useful in the therapy of different pathologies such as Parkinson's disease, renal failure, cardiac decompensation and hypertension.

However, for its high polarity and its fast metabolic inactivation, dopamine does not show pharmacokinetic characteristics that allow its absorption and distribution in the organism for the use in therapy.

Several attempts to prepare prodrugs of dopamine having pharmacokinetic characteristics that allow to improve the absorption of the active ingredient were carried out.

Among the prodrugs which may be used in therapy, there is gamma-L-glutamyl-L-dopa described for the first time in the British patent No. 1.598.016 (Mount Sinai School of Medicine of the City University of New York) which is a prodrug of dopamine particularly useful in the treatment of renal failure.

Even if this drug shows an interesting pharmacological activity, however, it has a serious limitation in its use in therapy for the lack of bioavailability by oral route and consequently, as reported by M. R. Lee, Serono Symposia Review No. 15—The peripheral Dopaminergic System, pages 79–88, (1988), there is the need to have analogues of gamma-L-glutamyl-L-dopa which do not undergo the hepatic first-pass and which release the active ingredient in the blood.

We have now surprisingly found new derivatives of gamma-L-glutamyl-L-dopa showing a high bioavailability by oral route.

Therefore, object of the present invention are compounds with the following general formula:

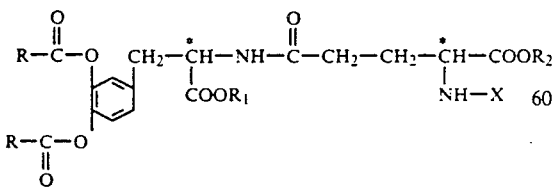
(I)

wherein
R is a linear or branched $C_1$–$C_7$ alkyl, a $C_1$–$C_5$ alkoxy, a phenyl or a 5- or 6-membered heterocycle having one to three hetero-atoms selected among oxygen, nitrogen and sulfur, optionally substituted by one to three substituents selected among halogen atoms, linear or branched $C_1$–$C_5$ alkyl, $C_2$–$C_5$ alkenyl, $C_1$–$C_5$ alkoxy or $C_2$–$C_5$ alkenyloxy groups, hydroxy, alkylcarbonyloxy, arylcarbonyloxy, amino, mono- or dialkylamino groups;
$R_1$ and $R_2$, the same or different, are a hydrogen atom or a linear or branched $C_1$–$C_5$ alkyl;
X is a hydrogen atom, a linear or branched $C_1$–$C_8$ alkanoyl or a benzoyl;
both the asymmetric carbon atoms, marked by an asterisk, having S configuration.

A further object of the present invention are the salts of the compounds of formula I with pharmaceutically acceptable acids or bases.

Examples of suitable acids are hydrochloric, hydrobromic, phosphoric, sulfuric, lactic, succinic, tartaric, acetic, salicyclic, citric, benzoic, p.hydroxybenzoic, naphthalen-2-sulfonic, adipic and pimelic acid.

Examples of suitable bases are sodium or potassium hydroxide, calcium or magnesium hydroxide, ethanolamine and tromethamol. The compounds of formula I are useful in the treatment of Parkinson's disease, renal failure, cardiac decompensation, and hypertension and they can be administered by oral route.

Preferred compounds of formula I are the compounds wherein R is a linear or branched $C_1$–$C_4$ alkyl, a $C_1$–$C_4$ alkoxy, a 5- or 6-membered heterocycle selected between pyridine and furan, a phenyl optionally substituted by one to three substituents selected among chlorine, bromine and fluorine atoms, methyl, ethyl, methoxy and ethoxy, a dimethylamino or a diethylamino; $R_1$, $R_2$ and X have the meanings reported for formula I.

More preferred compounds are those wherein R is methyl, ethyl, isopropyl, ethoxy, dimethylamino, phenyl, 4-methoxyphenyl; $R_1$ and $R_2$, the same or different, are hydrogen atoms, methyl, ethyl or isopropyl groups; X is a hydrogen atom or an acetyl group.

The preparation of the compounds of formula I, which is a further object of the present invention, is carried out by condensation between L-dopa or an ester thereof and a suitable derivative of L-glutamic acid according to the following reaction scheme:

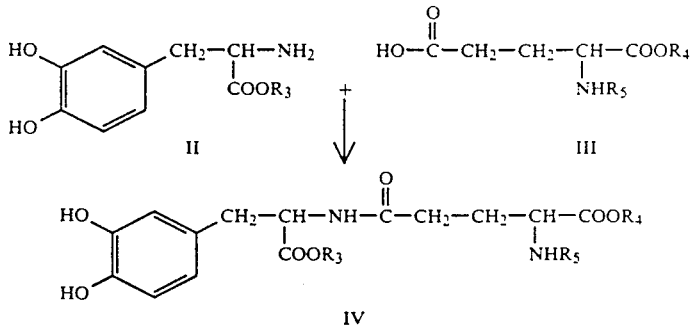

wherein
$R_3$ and $R_4$, the same or different, are a hydrogen atom, a linear or branched $C_1$–$C_5$ alkyl or a benzyl group;
$R_5$ is a protecting group, preferably t.butoxycarbonyl or benzyloxycarbonyl or it is a benzoyl or a $C_1$–$C_8$ alkanoyl.

The condensation reaction can be carried out on the intermediate III as such, by using condensing agents such as dicyclohexylcarbodiimide, as well as on a suitable reactive derivative of intermediate III.

Examples of suitable reactive derivatives are N-succinimido ester or mixed anhydrides with carbonic acid derivatives.

These reactive derivatives of intermediate III are prepared according to conventional techniques, optionally in situ before carrying out the condensation.

The condensation reaction between intermediate II and intermediate III or a reactive derivative thereof is carried out in an inert organic solvent and at a temperature between −40° C. and the room value.

As inert organic solvents, ethers such as tetrahydrofuran and dimethoxyethane or amides such as dimethylformamide are preferably used.

The compounds of formula IV are obtained and they are acylated and transformed into the compounds of formula I by removal of the protecting groups.

The acylation reaction is carried out by using a suitable derivative of a carboxylic or a carbonic acid of formula

RCOOH    (V)

wherein R has the above reported meanings.

Preferably the corresponding acyl chlorides are used as derivatives of the acid of formula V and the reaction is carried out in an acid organic solvent such as, for example, trifluoroacetic acid or in an inert organic solvent optionally in the presence of a base which may act also as a solvent.

The removal of the protecting groups can be carried out by treatment with acids or by hydrogenation.

Alternatively, the deprotection reaction can be carried out on the intermediate IV, that is before the acylation reaction.

The compounds of formula I object of the present invention are absorbed by oral route and they regenerate metabolically dopamine producing useful pharmacological effects by stimulation of dopaminergic receptors.

The compounds of formula I can be used in the therapy of Parkinson's disease and in the therapy of cardiovascular diseases such as cardiac decompensation, hypertension and renal failure. In particular, the compounds object of the present invention are able to increase the renal blood flow.

The pharmacological activity of the compounds of formula I was tested in awake beagle dogs cronically instrumented with an electromagnetic flow probe on left renal artery and catheter in abdominal aorta.

The animals weighing 11-12 kg of both sexes were anesthetized with sodium pentobarbital 30 mg/kg i.v. and under sterile conditions a left renal artery was exposed through a retroperitoneal access. An electromagnetic flow probe as well as a pneumatic occluder were placed around the artery in order to measure renal blood flow (RBF) and to make the mechanical zero flow.

A catheter was introduced into the abdominal aorta and advanced into ascending aorta in order to measure systemic blood pressure (BP).

The catheter and the flow probe were exteriorized on the neck. After 10-15 day recovery period the compounds of the present invention were tested for their renal vasodilator activity by oral administration.

RBF and BP were recorded before and at fixed intervals after treatment up to 6 hours. Heart rate was also determined by BP tracing and renal vascular resistance (RVR) was calculated as ratio of BP to RBF.

The compounds of formula I, object of the present invention, administered in a range of doses of 5-100 mg/kg orally have been shown to produce a selective renal vasodilator activity since RBF increased and RVR decreased whereas BP and heart rate did not significantly change.

A further object of the present invention are the pharmaceutical compositions containing one or more compounds of formula I or their pharmaceutically acceptable salts optionally in a mixture with one or more excipients suitable for pharmaceutical use.

The compositions object of the present invention can be solid, such as tablets, granulates, capsules, coated tablets or liquid such as solutions, syrups, emulsions and they are prepared according to conventional techniques.

They can be administered by enteral as well as by parenteral route.

The preferred administration route is the oral route.

The doses may change depending on the selected pharmaceutical preparation and on the individual answer of the patient but they are generally between 100 mg and 5 g a day.

In order to better illustrate the present invention without limiting it, the following example are now given.

EXAMPLE 1

Preparation of (N-benzyloxycarbonyl-L-gamma-glutamyl)-3,4-dihydroxy-L-phenylalanine diethyl ester Triethylamine (38.6 ml; 0.27 moles) and, then, N-benzyloxycarbonyl-O$^5$-succinimido-L-glutamic acid ethyl ester (102.5 g; 0.25 moles) were added to a solution of 3,4-dihydroxy-L-phenylalanine ethyl ester hydrochloride (66 g; 0.25 moles) in dimethylformamide (600 ml).

After an hour at room temperature, the reaction mixture was diluted with water and extracted with ethyl acetate.

The organic phase was washed with water, dried on sodium sulfate, filtered and evaporated.

The residue was purified by column chromatography on silica gel, eluent methylene chloride mixed with increasing amounts of methanol up to 5%.

(N-benzyloxycarbonyl-L-gamma-glutamyl)-3,4-dihydroxy-L-phenylalanine diethyl ester was obtained as a pure oil by thin layer chromatography (eluent $CH_2Cl_2$: methanol: water=97:7.5:0.5, detection U.V. light, $I_2$ vapours).

$^1$H-NMR (300 MHz, $CDCl_3$) delta (ppm): 1.27 (3H, t); 1.29 (3H, t); 1.8 (1H, m); 2.28-4.43 (3H, m); 2.95 (1H, dd); 3.16 (1H, dd); 4.17-4.23 (4H, m); 4.32 (1H, m); 4.79 (1H, m); 5.12 (2H, d); 6.35 (1H, d); 6.48 (1H, dd); 6.69 (1H, d); 7.34 (5H, s).

By working in a similar way the following compounds were obtained:

(N-benzyloxycarbonyl-L-gamma-glutamyl-alfa-benzyl ester)-3,4-dihydroxy-L-phenylalanine ethyl ester as a pure oil by thin layer chromatography (eluent $CH_2Cl_2$: methanol: water=97:7.5:0.5, de-detection U.V. light, $I_2$ vapours).

$^1$H-NMR (300 MHz, $CDCl_3$) delta (ppm): 1.26 (3H, t); 1.78-1.98 (1H, m); 2.17-2.30 (3H, m); 2.90 (1H, dd); 3.06 (1H, dd); 4.16 (2H, q); 4.29-4.36 (1H, m); 4.73-4.80

(1H, m); 5.04–5.20 (6H, m); 6.48 (1H, dd); 6.68 (1H, d); 6.75 (1H, d); 7.35 (10H, s).

(N-benzyloxycarbonyl-L-gamma-glutamyl-alfa-ethyl ester)-3,4-dihydroxy-L-phenylalanine benzyl ester as a pure oil by thin layer chromatography (eluent $CH_2Cl_2$: toluene: methanol=25:5:2, detection U.V. light, $I_2$ vapours).

$^1$H-NMR (300 MHz, $CDCl_3$) delta (ppm): 1.29 (3H, t); 1.72–1.84 (1H, m); 2.21–2.52 (3H, m); 2.83 (1H, dd); 3.17 (1H, dd); 4.22 (2H, q); 4.34 (1H, dt); 4.82–4.88 (1H, m); 5.10–5.20 (4H, m); 6.27 (1H, dd); 6.64 (1H, d); 6.66 (1H, d); 7.29–7.42 (10H, m).

(N-benzyloxycarbonyl-L-gamma-glutamyl)-3,4-dihydroxy-L-phenylalanine dibenzyl ester as a pure oil by thin layer chromatography (eluent $CH_2Cl_2$: toluene: methanol=25:5:5, detection U.V. light, $I_2$ vapours).

$^1$H-NMR (300 MHz, $CDCl_3$) delta (ppm): 1.75–1.88 (1H, m); 2.18–2.37 (3H, m); 2.88–3.12 (2H, m); 4.31–4.39 (1H, m); 4.80–4.86 (1H, m); 5.06–5.22 (6H, m); 6.27 (1H, dd); 6.60 (1H, d); 6.66 (1H, d); 7.28–7.40 (15H, m).

EXAMPLE 2

Preparation of L-gamma-glutamyl-3,4-dihydroxy-L-phenylalanine diethyl ester

A suspension of (N-benzyloxycarbonyl-L-gamma-glutamyl)-3,4-dihydroxy-L-phenylalanine diethyl ester (70 g; 0.135 moles), prepared as described in example 1, and 10% palladium on charcoal (7 g) in ethyl alcohol (0.5 l) was kept under 2–3 atmospheres hydrogen pressure at room temperature.

After the theoric hydrogen absorption, the reaction mixture was filtered and the solvent was evaporated.

L-gamma-glutamyl-3,4-dihydroxy-L-phenylalanine diethyl ester was obtained as a pure oil by thin layer chromatography (eluent methylene chloride: methanol: acetic acid=79:15:1, detection U.V. light, $I_2$ vapours) and used in the next step without any further purification.

$^1$H-NMR (300 MHz, DMSO-$d_6$) delta (ppm): 1.12 (3H, t); 1.18 (3H, t); 1.49–1.83 (2H, m); 2.18 (2H, t); 2.65–2.82 (2H, m); 3.12 (1H, dd); 3.98–4.10 (4H, m); 4.25–4.32 (1H, m); 6.42 (1H, dd); 6.58 (1H, d); 6.60 (1H, d).

By working in a similar way the following compound was obtained:

(L-gamma-glutamyl)-3,4-dihydroxy-L-phenylalanine ethyl ester m.p. 130°–140° C. with decomposition (ethyl ester)

$^1$H-NMR (300 MHz, DMSO-$d_6$) delta (ppm): 1.10 (3H, t); 1.79–1.92 (2H, m); 2.20–2.34 (2H, m); 2.67–2.84 (2H, m); 3.32–3.42 (1H, m); 3.99–4.09 (2H, m); 4.26 (1H, q); 6.43 (1H, dd); 7.12 (2H, d).

EXAMPLE 3

Preparation of (L-gamma-glutamyl)-[3,4-di-(4-methoxybenzoyloxy)-L-phenylalanine]diethyl ester hydrochloride 4-methoxybenzoyl chloride (4.81 g; 28.2 mmoles) was added to a solution of (L-gamma-glutamyl)-3,4-dihydroxy-L-phenylalanine diethyl ester (3.6 g; 9.4 mmoles), prepared as described in example 2, in trifluoroacetic acid (36 ml).

After an hour at room temperature the reaction mixture was evaporated.

After purification by column chromatography on silica gel (eluent $CH_2Cl_2$: methanol: acetic acid=92:7.5:0.5), the obtained pure product was dissolved in ethanol saturated with hydrochloric acid. The solution was evaporated to dryness and the residue was crystallized from acetonitrile/isopropyl ether giving (L-gamma-glutamyl)-[3,4-di-(4-methoxybenzoyloxy)-L-phenylalanine]diethyl ester hydrochloride (m.p. 179°–181° C.).

$^1$H-NMR (300 MHz, DMSO-$d_6$) delta (ppm): 1.15 (3H, t); 1.27 (3H, t); 1.98 (2H, q); 2.32–2.42 (2H, m); 2.96–3.15 (2H, m); 3.78 (6H, 2s); 3.96 (1H, t); 4.07 (2H, q); 4.17 (2H, q); 4.45–4.54 (1H, q); 7.00 (4H, dd); 7.26 (1H, dd); 7.35 (1H, d); 7.38 (1H, d); 7.88 (4H, dd).

By working in a similar way the following compounds were obtained:

(L-gamma-glutamyl)-(3,4-diacetyloxy)-L-phenylalanine diethyl ester hydrochloride m.p. 166°–168° C. (isopropanol/isopropyl ether)

$^1$H-NMR (300 MHz, DMSO-$d_6$) delta (ppm): 1.02 (3H, t); 1.14 (3H, t); 1.97 (2H, q); 2.27 (6H, 2s); 2.22–2.40 (2H, m); 2.99–3.06 (2H, m); 3.99 (1H, t); 4.03 (2H, q); 4.18 (1H, q); 4.43 (1H, q); 7.15 (3H, d).

(L-gamma-glutamyl)-(3,4-diisobutyryloxy)-L-phenylalanine diethyl ester hydrochloride m.p. 118°–119° C. (isopropanol/isopropyl ether)

$^1$H-NMR (300 MHz, DMSO-$d_6$) delta (ppm): 1.02 (3H, t); 1.10 (15H, m); 1.97 (2H, q); 2.22–2.48 (2H, octet); 2.78 (2H, two septets); 2.88–3.07 (2H, m); 2.94 (1H, t); 4.04 (2H, q); 4.18 (2H, q); 4.43 (1H, q); 7.16 (3H, d).

(L-gamma-glutamyl)-(3,4-diisobutyryloxy)-L-phenylalanine ethyl ester hydrochloride m.p. 85°–90° C. with decomposition $^1$H-NMR (300 MHz, DMSO-$d_6$) delta (ppm); 1.10 (3H, t); 1.21 (6H, 2d); 1.90–2.00 (2H, m); 2.22–2.35 (2H, m); 2.79 (2H, two quintets); 2.99–3.05 (2H, m); 3.78 (1H, t); 4.02 (2H, q); 4.42 (1H, q); 7.12–7.16 (3H, m).

(N-benzyloxycarbonyl-L-gamma-glutamyl-alfa-ethyl ester -[3,4-di-(4-methoxybenzoyloxy)-L-phenylalanine]-benzyl ester m.p. 127°–130° C. (methylene chloride/ethyl ether)

$^1$H-NMR (300 MHz, $CDCl_3$) delta (ppm): 1.22 (3H, t); 1.88–2.00 (1H, m); 2.13–2.43 (3H, m); 3.10–3.25 (2H, m); 3.83 (3H, s); 3.85 (3H, s); 4.16 (2H, q); 4.30 (1H, sextet); 4.94 (1H, q); 5.08–5.26 (4H, m); 6.80–6.87 (4H, m); 6.92 (1H, dd); 7.08 (1H, d); 7.17 (1H, d); 7.26–7.37 (10H, m); 7.97–8.02 (4H, 2d).

EXAMPLE 4

Preparation of (N-benzyloxycarbonyl-L-gamma-glutamyl)-[3,4-di-(N,N-dimethylcarbamoyloxy)-L-phenylalanine]dibenzyl ester N,N-dimethylcarbamoylchloride (17.2 ml; 187 mmoles) and N,N-dimethylaminopyridine (100 mg) were added to a solution of (N-benzyloxycarbonyl-L-gamma-glutamyl)-3,4-dihydroxy-L-phenylalanine dibenzyl ester (20 g; 31.2 mmoles), prepared as described in example 1, in pyridine (100 ml).

After 5 hours at 45°–50° C. and 48 hours at room temperature, the reaction mixture was evaporated to dryness; the residue was dissolved in ethyl acetate, washed with water, with 0.5N hydrochloric acid and then with water.

The organic phase was dried on $Na_2SO_4$ and evaporated.

The product was purified by chromatography on silica gel (eluent methylene chloride: methanol=97:3) giving (N-benzyloxycarbonyl-L-gamma-glutamyl)-[3,4- di-(N,N-dimethylcarbamoyloxy)-L-phenylalanine]dibenzyl ester as a pure oil by thin layer chromatography (eluent CH$_2$Cl$_2$: toluene: methanol=25:5:2, detection U.V. light, I$_2$ vapours).

$^1$H-NMR (300 MHz, CDCl$_3$) delta (ppm): 1.85–2.28 (4H, m); 209–3.15 (14H, m); 4.27–4.35 (1H, m); 4.82–4.90 (1H, m); 5.20–5.28 (6H, m); 6.74 (1H, dd); 6.98 (1H, d); 7.02 (1H, d); 7.25–7.41 (15H, m).

EXAMPLE 5

Preparation of (L-gamma-glutamyl-alpha-ethyl ester)-[3,4-di-(4-methoxybenzoyloxy)-L-phenylalanine]

A suspension of (N-benzyloxycarbonyl-L-gamma-glutamyl-alpha-ethyl ester)-[3,4-di-(4-methoxybenzoyloxy)-L-phenylalanine]benzyl ester (14 g; 16.1 mmoles), prepared as described in example 3, and 10% palladium on charcoal (1.4 g) in a mixture 95% ethanol: tetrahydrofuran=9:1 (155 ml) was kept under 2–3 atmospheres hydrogen pressure at room temperature.

After the theoric hydrogen absorption, the catalyst was filtered off and washed with ethanol.

The solution was concentrated up to half volume and, by cooling, (L-gamma-glutamyl-alpha-ethyl ester)-[3,4-di-(4-methoxybenzoyloxy)-L-phenylalanine] separated.

m.p. 162°–164° C.

$^1$H-NMR (300 MHz, DMSO-d$_6$) delta (ppm): 1.08 (3H, t); 1.68 (1H, sextet); 1.88 (1H, sextet); 2.13–2.30 (2H, m); 2.92 (1H, dd); 3.15 (1H, dd); 3.41 (1H, dd); 3.80 (6H, s); 4.08 (2H, q); 4.34–4.41 (1H, m); 6.99 (4H, 2d); 7.23 (1H, dd); 7.29 (1H, d); 7.32 (1H, d); 7.88–7.92 (4H, 2d).

By working in a similar way the following compound was obtained:

(L-gamma-glutamyl)-[3,4-di-(N,N-dimethylcarbamoyloxy)-L-phenylalanine]

m.p. 125°–140° C. (with slow decomposition)

$^1$H-NMR (300 MHz, D$_2$O) delta (ppm): 2.05 (2H, m); 2.42 (2H, t); 2.98 (6H, s); 3.06 (1H, m); 3.08 (6H, s); 3.28 (1H, dd); 3.82 (1H, t); 4.62–4.73 (1H, m); 7.15–7.21 (3H, m).

EXAMPLE 6

Preparation of (N-acetyl-L-gamma-glutamyl)-(3,4-diisobutyryloxy)-L-phenylalanine diethyl ester A solution of (L-gamma-glutamyl)-(3,4-diisobutyryloxy)-L-phenylalanine diethyl ester hydrochloride (2.8 g; 5 mmoles), prepared as described in example 3, triethylamine (0.696 ml; 5 mmoles) and acetic anhydride (4.73 ml; 50 mmoles) in chloroform (28 ml) was kept under stirring at room temperature for 30 minutes.

After evaporation of the solvent, the residue was treated with water and (N-acetyl-L-gamma-glutamyl)-3,4-diisobutyryloxy)-L-phenylalanine diethyl ester separated.

m.p. 138°–139° C.

$^1$H-NMR (300 MHz, CDCl$_3$) delta (ppm): 1.21–1.32 (18H, m); 1.85–1.96 (1H, m); 2.02 (3H, s); 2.06–2.18 (1H, m); 2.28 (2H, octet); 2.75 (2H, two quintets); 3.04–3.18 (2H, m); 4.17 (4H, 2q); 4.41–4.48 (1H, m); 4.82 (1H, q); 6.94–7.08 (3H, m).

What we claim is:

1. A compound of formula

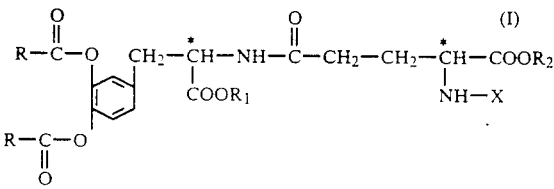

wherein

R is methyl, ethyl, isopropyl, ethoxy, dimethylamino, phenyl, or 4-methoxyphenyl;

R$_1$ and R$_2$, the same or different, are hydrogen atoms, or methyl, ethyl or isopropyl groups; and X is a hydrogen atom or an acetyl group;

both the asymmetric carbon atoms, marked by an asterisk, having S configuration;

and salts thereof with pharmaceutically acceptable acids or bases.

2. A pharmaceutical composition containing one or more compounds according to claim 1 in a mixture with one or more excipients suitable for pharmaceutical use.

3. A method for the treatment of Parkinson's disease consisting in administering a therapeutically effective amount of a compound according to claim 1.

4. A method for the treatment of cardiovascular diseases consisting in administering a therapeutically effective amount of a compound according to claim 1.

* * * * *